(12) United States Patent
Rickwood

(10) Patent No.: US 6,344,357 B1
(45) Date of Patent: Feb. 5, 2002

(54) TREATING CELLS

(75) Inventor: David Rickwood, Colchester (GB)

(73) Assignee: Immunoporation LTD (GB)

( * ) Notice: Subject to any disclaimer, the term of this patent is extended or adjusted under 35 U.S.C. 154(b) by 0 days.

(21) Appl. No.: 09/719,325

(22) PCT Filed: Jun. 10, 1999

(86) PCT No.: PCT/GB99/01845

§ 371 Date: Feb. 9, 2001

§ 102(e) Date: Feb. 9, 2001

(87) PCT Pub. No.: WO99/64575

PCT Pub. Date: Dec. 16, 1999

(51) Int. Cl.⁷ ............................................... C12N 15/64
(52) U.S. Cl. .................... 435/455; 435/459; 530/387.1; 530/388.1; 530/388.22; 530/389.1; 530/391.1
(58) Field of Search ................................. 435/455, 459; 530/387.1, 388.1, 388.22, 389.1, 391.1

(56) References Cited

PUBLICATIONS

"The Mechanism of Osmotic Transfection of Avian Embryonic Erythrocytes: Analysis of a System for Studying Developmental Gene Expression," M.R. Lieber et al., *Journal of Cell Biology*, vol. 105, 1987, pp. 1055–1065.

"The Laser Method for Efficient Introduction of Foreign DNA into Cultured Cells," S. Kurata et al., *Experimental Cell Research*, vol. 162, 1986, pp. 372–378.

"Laser–Mediated Gene Transfer in Rice," Y. Guo et al., *Physiologia Plantarum*, vol. 93, 1995, pp. 19–24.

"Evidence of Surface Antigen Detachment During Incubation of Cells with Immunomagnetic Beads," C.P. Rubbi et al, *Journal of Immunological Methods*, vol. 166, 1993, pp. 233–241.

*Primary Examiner*—James Ketter
(74) *Attorney, Agent, or Firm*—Carmody & Torrance LLP

(57) ABSTRACT

Provided is a method for introducing a substance into a cell, which method comprises: (a) contacting the cell with a recognition agent to bind the recognition agent to a recognition site on the surface of the cell; and (b) separating the recognition agent from the cell thereby forming a hole in the surface of the cell. Kits for use in such methods are also provided.

46 Claims, 3 Drawing Sheets

TREATING CELLS

Figure 1:
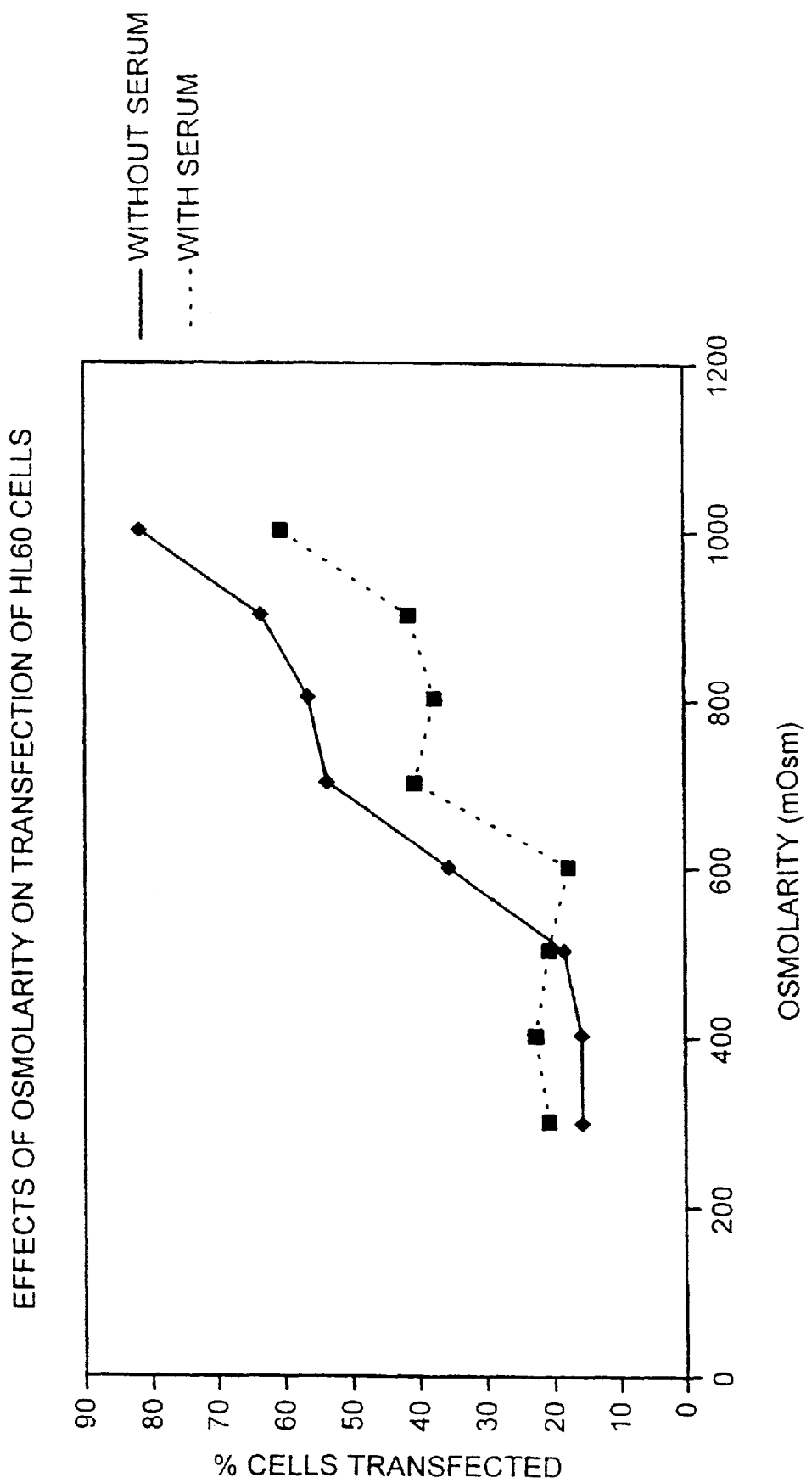

The present invention relates to a method for introducing a substance into a cell, and in particular to an efficient transfection method involving a low incidence of cell-death. The invention also relates to kits for introducing a substance into a cell.

Throughout this text, the introduction of foreign substances, such as nucleic acid protein, peptides or other biological molecules into cells is termed transfection. Transfection, particularly of genetic material, has recently proved to be one of the most important techniques in molecular biology, particularly in relation to genetic engineering and protein engineering. The technique has allowed foreign DNA to be expressed in cells. This is of scientific interest in studying gene transcription and has a wide range of commercial applications involving expressing commercially useful gene products in convenient types of cell. More recently there has been interest in introducing both proteins and drugs into living cells without damaging the cells. A significant problem to be overcome when developing such techniques is the general imperviousness of the cell membrane. The cell membrane is normally impervious to even small molecules, unless they are very lipophilic. Even short-term damage to the cell membrane to render it more permeable tends to result in cell-death. This is a particular problem associated with electroporation, discussed below.

A number of methods have been devised for transfecting cells with foreign DNA or other substances. Early methods involved binding DNA to particles such as diethylaminoethyl (DEAE) cellulose or hydroxyapatite and adding pretreated cells which are capable of taking up particles containing DNA. These early methods are very inefficient, the level of transfection achievable being very low.

More recently methods have been developed which make use of liposomes loaded with DNA that can be fused with cells. A further technique involves subjecting cells, typically plant cells, to an electric shock which causes the formation of holes in the cells. This method is termed electroporation.

In Biotechniques, Vol 17 No. 6 1994, page 118–1125, Clarke et al. disclose a method for introducing dyes, proteins and plasmid DNA into cells using an impact-mediated procedure. In this method, compressed gas is used to propel glass beads dispersed as a uniform aerosol onto adherent cells growing on a culture substratum. The impact of beads on the cells creates plasma membrane wounds. Molecules such as dyes, proteins and plasmid DNAs diffuse from the extracellular environment directly into the cytoplasmic compartment of the cell through the wounds.

In *Nucleic Acids Research*, Vol. 18, No. 21, 1990, p.6464, the effect of the osmolarity of the transfection medium is studied in relation to electroporation methods. It was reported that the optimum osmolarity of the transfection medium for transfection by electroporation is around 300 mOsm.

A significant problem associated with the above treatments is that they are very inefficient. In addition, a large proportion of the cells are killed by the above treatments. Moreover, the treatments are not selective. In fact, no methods are presently available for the selective transfection of cells. Furthermore, in the method of Clarke et al, only a limited number of cells can be transfected in a single treatment.

An object of the present invention is to overcome the above drawbacks and to provide an efficient method of transfection with good cell survival rates and the possibility of selective transfection of a sub-population of cells in a sample. Accordingly, the present invention provides a method for introducing a substance into a cell, which method comprises:

(a) contacting the cell with a recognition agent to bind the recognition agent to a recognition site on the surface of the cell; and (b) separating the recognition agent from the cell thereby forming a hole in the surface of the cell.

The method of the invention is conveniently referred to herein, as "immunoporation", although not all methods of the invention actually involve any immunological components or interactions.

The cell can be contacted with the substance to be introduced simultaneously with the formation of the hole in step (b), or alternatively in a subsequent separate step. Introduction of the substance may thus occur as a result of contact of the substance with the cell which contains one or more holes which facilitate passage of the substance into the cell. This said hole allows passage into the cell membrane or more preferably the cytoplasm of the cell.

The hole formed is typically transient in that it only exists for a very short period before the cell membrane again forms a substantially continuous layer. The important characteristic of the hole is that it enables the substance which it is intended to introduce into the cell to pass from the outside to the inside of the cell.

Figure 2:
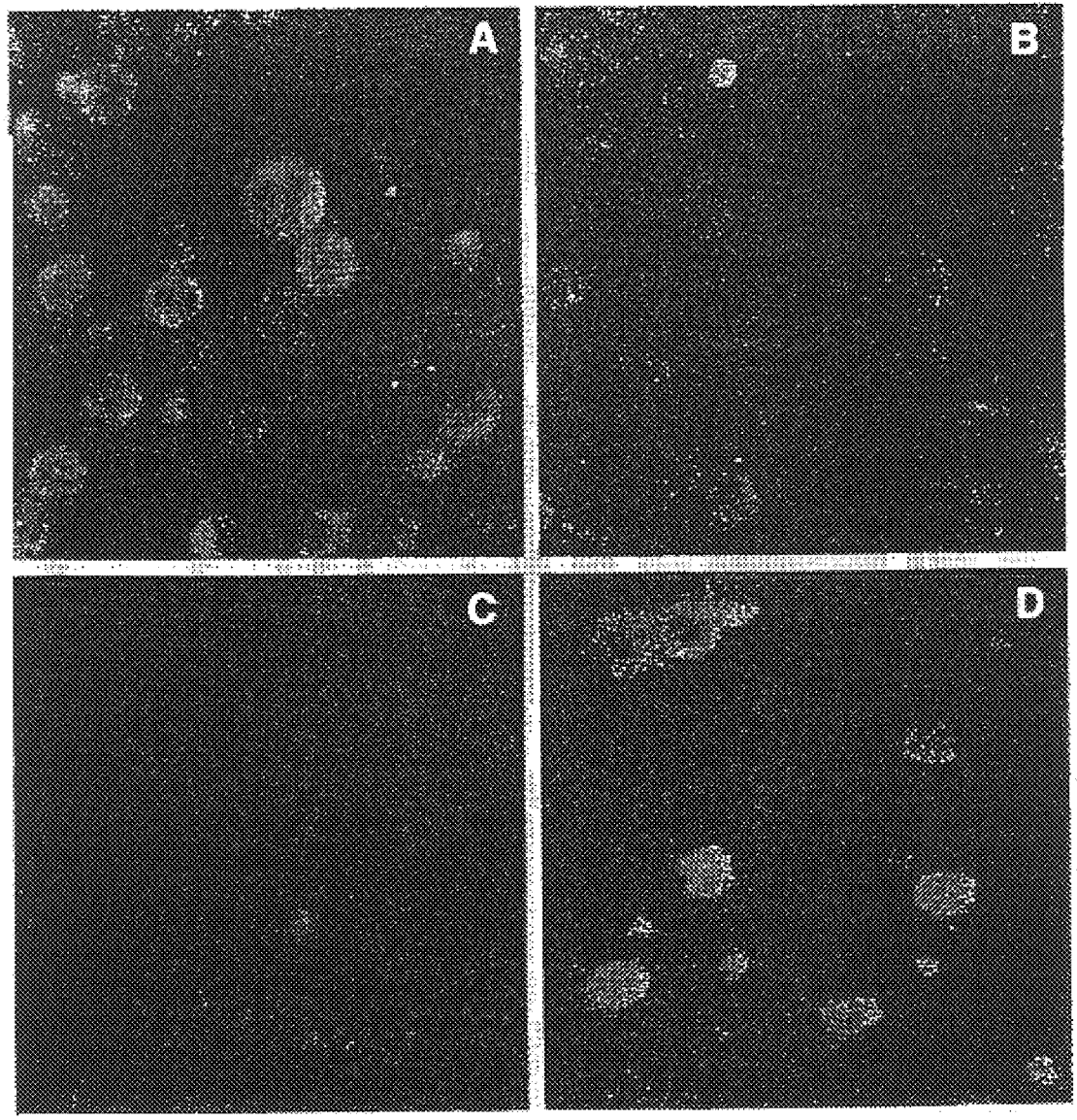
Figure 3:
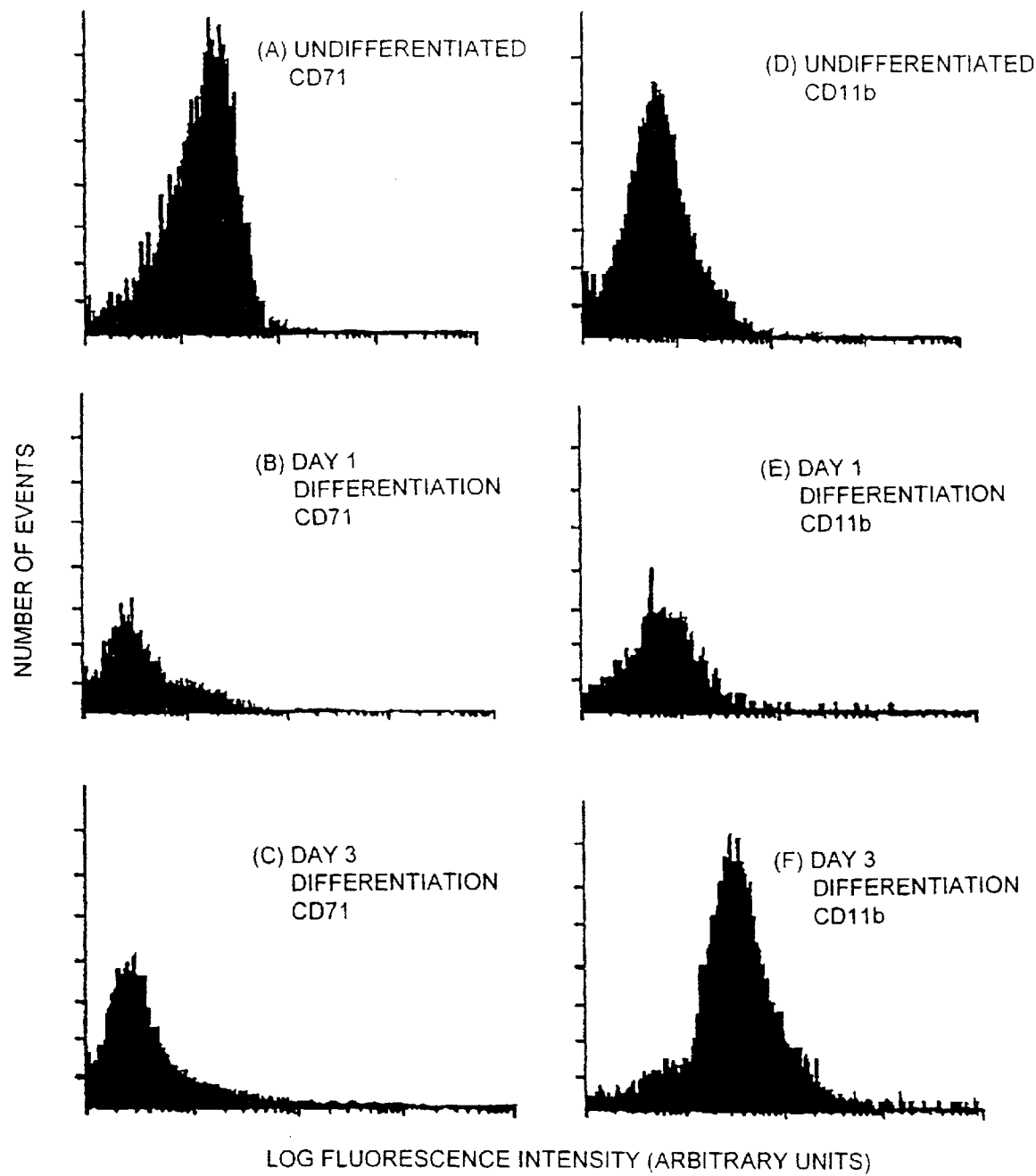

The invention will now be described in further detail by way of example only, with reference to the accompanying drawings, in which:

FIG. 1 shows the effect of the osmolarity of the transfection medium on the transfection of HL60 cells;

FIG. 2 shows confocal images of (A) promyelocytic HL-60 cells transfected with TMR-dextran using anti-CD71-coated Dynafect beads, (B) promyelocytic HL-60 cells transfected with TMR-dextran using anti-CD11b-coated Dynafect beads (negative control), (C) 3 day DMSO differentiated HL-60 cells transfected with TMR-dextran using anti-CD71-coated Dynafect beads (negative control), (D) 3 day DMSO differentiated HL-60 cells transfected with TMR-dextran using anti-CD11b-coated Dynafect beads; and FIG. 3 shows FACS analysis of the expression of GFP in: (A) promyelocytic HL-60 cells transfected with pEGFP-C1 using anti-CD71-coated Dynafect beads, (B) HL-60 cells transfected with pEGFP-C1 using anti-CD71-coated Dynafect beads 1 day after induction with DMSO, (C) HL-60 cells transfected with pEGFP-C1 using anti-CD71-coated Dynafect beads 3 days after induction with DMSO, (D) promyelocytic HL-60 cells transfected with pEGFP-C1 using anti-CD11b-coated Dynafect beads, (E) HL-60 cells transfected with pEGFP-C1 using anti-CD11b-coated Dynafect beads 1 day after induction with DMSO and (F) HL-60 cells transfected with pEGFP-C1 using anti-CD11b-coated Dynafect beads 3 days after induction with DMSO.

The step (b) of the present method is preferably carried out in a liquid medium. In the present context this is termed an immunoporation medium. To maximise the efficiency and rate of transfection, the liquid medium used to transfect the cells typically has an osmolarity of from 0.1–4.0 times the osmolarity of the cells. In the context of the present invention, the osmolarity of the cell means the normal osmolarity of the untreated cell. Preferably, the liquid medium has an osmolarity of from 30–1200 mOsm. When the cells to be transfected are adherent, the osmolarity of the liquid medium is preferably less than the osmolarity of the cells, more preferably from 30–150, e.g. 40–100 mOsm and most preferably from 40–50 mOsm. When the cells to be transfected are in the form of a suspension, the osmolarity of the liquid medium is preferably greater than the osmolarity of the cells, more preferably from 700–1100 mOsm, more preferably still from 800–1000 mOsm and most preferably from 950–1000 mOsm. Thus non-isotonic conditions, relative to the osmolarity of the cells, allows for most efficient immunoporation and the liquid medium will therefore preferably not be isotonic or approximately isotonic having regard to the osmolarity of the cells.

The osmolarity of a liquid medium is a measure of the concentration of ions in the medium. The ions present in the immunoporation medium are not limited to a particular type of ion, provided that they do not inhibit transfection and can be tolerated by the cells. An immunoporation medium having the desired osmolarity may be formulated using 10 times concentrated Earl's balanced salt solution (EBSS) (Earl, W. R., 1934, Arch. Exp. Zell. Forsch., Vol. 16, p. 116) containing nutrient factors as a base and diluting as required.

In the present invention, any recognition agent can be used as long as it is capable of binding with a recognition site on the cell surface. A recognition agent and/or a recognition site may comprise one or more molecules which together comprise the site of affinity binding, e.g. the recognition site may be a receptor complex to which a ligand may be bound. In the context of the present invention, such pairs of recognition agents and recognition sites capable of binding to form complexes are termed "recognition pairs". Recognition pairs may be any pair of substances which have an affinity for one another, that is any pair of substances which are affinity binding partners e.g. bind to one another selectively under physiological pH and ionic conditions. Preferably recognition pairs are of the ligand/receptor type, i.e. pairs of agents in which the ligand has a structure that is specific for a given receptor (e.g. an antibody/antigen-type interaction). However, the pairs may also have a more conventional chemical binding mechanism such as a covalent, ionic, hydrophobic or hydrogen bonding interaction. Thus cell adhesion molecules are also envisaged as recognition pairs.

When the recognition pair has a ligand/receptor-type interaction, the recognition site on the cell surface may be either the receptor, or the ligand and the recognition agent may thus be either the ligand or the receptor.

In a preferred embodiment of the present invention, the recognition agent is selected from an antibody, an antigen, a growth factor, a growth factor receptor, a sugar, a sugar receptor, a hormone, a hormone receptor, a cell adhesion molecule, an enzyme, an enzyme substrate, a co-enzyme, a protein, a synthetic ligand, a synthetic receptor, a phage, a phage receptor, and a molecule capable of binding to any of the above. More preferably, the recognition pair employed in the present invention is selected from the following complexes:

(i) an antibody/antigen complex, (ii) a growth factor/growth factor receptor complex, (iii) a sugar/sugar receptor complex, (iv) a hormone/hormone receptor complex, (v) a complex formed from cell adhesion molecules, (vi) an enzyme/substrate complex, (vii) an enzyme/co-enzyme complex, (viii) a lectin/lectin receptor complex, (ix) a protein/organic molecule complex, (x) a synthetic ligand/synthetic receptor complex, and (xi) a phage/phage receptor complex.

When the recognition pair is an antibody/antigen complex, there is no particular limitation on the type of antibody or antigen used. The antibody may be polyclonal or monoclonal, synthetic (such as chimeric antibodies) or single chain antibodies. Fragments of antibodies, such as $F_v$ or Fab fragments may also be used. The antigens may include antigen fragments and haptens. Preferably the receptor is an HLA Class I and the ligand is an anti Class I antibody. Antibodies can be species specific, provided that the appropriate epitope and antibody-type are selected, such that the antibody recognises only one particular epitope.

A growth factor/receptor recognition pair preferred in the present invention is the EGF(epidermal growth factor)/EGF receptor complex. This growth factor receptor is expressed at high levels in certain tumour cells, such that using the growth factor leads to enhanced transfection of such tumour cells.

The mannose/mannose receptor complex is a preferred sugar/sugar receptor complex in the present invention. The advantage of mannose as a recognition agent is that the mannose receptor is present on the surface of macrophage cells. Mannose is thus useful in selectively transfecting macrophage cells in the presence of cells which do not have a mannose receptor on their surface.

An example of a preferred hormone/hormone receptor complex employed in the present invention is the insulin/insulin receptor complex. Insulin is useful as a recognition agent, since the insulin receptor is present on the surface of liver cells. Insulin is thus useful in selectively transfecting liver cells in the presence of cells which do not have an insulin receptor on their surface.

Oligosaccharides are preferred in the present invention as cell adhesion molecules. Specific oligosaccharide/selectin complexes have the advantage of being selective for specific tissues, depending on the oligosaccharide/selectin complex employed.

One enzyme/substrate recognition pair envisaged for use in the present invention is the 5'-AMP(adenylic acid, or analogue)/5'nucleotidase complex. This complex is generic for all cells and could be employed to transfect all cells in a sample, when selectivity is not important. A preferred enzyme/co-enzyme recognition pair is the $NAD^+$ (nicotinamide adenine dinucleotide)/dehydrogenase complex, genetically engineered so that the dehydrogenase is on the cell surface.

An example of a protein/protein-binding molecule complex for use in the present invention is the avidin/biotin complex. However, any molecule which, like biotin, (in particular an organic molecule) is capable of binding to one of the ligands or receptors described above will be useful in the present invention. In addition to a protein/protein binding molecule, a peptide/(peptide or protein) binding molecule could be employed. The peptide may be, for example, a peptide from a peptide library.

Synthetic ligands and synthetic receptors can, in a preferred embodiment of the present invention, be genetically modified (GM) ligands and receptors. These types of recognition pair are particularly useful, since the GM ligand can be designed to be specific to a particular GM cell having a GM receptor on it surface.

The recognition pairs are not limited to the specific examples listed above, and in general may include any biological effector molecules, of which hormones and growth factors are merely examples. Since the method of the invention may be used to selectively transfect cells bearing a particular recognition site, it will be appreciated that preferred recognition sites are those which a re present on a sub-set of cells and which are an indication of a particular cell type or an indicator of adherent cells e.g. tumour cells or modified cells expressing e.g. a mutant surface protein.

The recognition sites expressed on the surface of cells of a discrete lineage or on abherant or diseased cells are preferred.

Given that the methods of the invention involve forming holes in the cell membrane, changes in the behaviour of the membrane can affect the efficiency of transfection. The fluidity of membranes is very temperature dependent, and it has been found using the standard mixing conditions (see the Examples) that the level of transfection which could be achieved at 10° C. was significantly less than that obtained at room temperature (22° C.). At 30° C., although good levels of transfection could be achieved, there was also a large increase in the non-specific binding of the transfection molecules to the cell surface. Thus, generally, preferred transfection temperatures will be in the region of 18 to 28° C.

The present method has many advantages. For example, when using an antibody, the antibody can be made selective for antigens specific to certain types of cells. Accordingly, in a cell population containing a number of different cells, specific types of cells can be targeted for transfection in preference to other types of cells. Moreover, there is no significant decrease in the viability of the cells, even when large amounts of cell surface are removed. The holes formed in the cells are transient, remaining open for a sufficient time to allow the influx of macromolecules into the cell, but re-sealing before the viability of the cell is compromised. For instance, using the method of the present invention, cell-death is generally less than 25% and often less than 5%. On the other hand, if electroporation is used cell-death can sometimes be as high as 90%.

In the present method, the recognition agent is separated from the cell by introducing a force between the cell and the recognition agent. In a preferred embodiment, the force is created by perturbing a liquid medium containing the cell and the recognition agent. However, the liquid medium may alternatively be allowed to flow across the surface of the solid on which the cell is isolated. The force set up is such that access to the inside of the cell is created by ripping or tearing a transient hole in the cell surface.

The hole in the cell surface may be a rip or tear in the cell membrane and may also include a hole formed by entirely removing a portion of the cell membrane. The recognition agent alone may be removed from the cell (i.e. the bond between the recognition pair is broken and the recognition site remains on the surface of the cell), provided that the cell surface is stressed sufficiently to tear or rip a hole in its surface. More preferably the bound recognition pair complex is removed from the cell, optionally together with part of the cell membrane, comprising either the phospholipid bi-layer, other membrane proteins or both.

It is preferred that the recognition agent is attached to the surface of a solid prior to contacting it with the cell. Suitable solids are well known in the art and include particles e.g. beads, and non-particulate materials such as a solid surface of any type such as the surface of sheets, gels, filters, membranes, fibres, capillaries, tubes, plates, dishes and wells. The support may conveniently be made of glass, silica, latex, a polymeric material or a magnetic or magnetisable material. A single recognition agent may be attached to one surface, typically when the solid surface is a bead. However, a plurality of recognition agents may also be attached to the surface of the same solid, such as the surface of a bead, a well, or a test tube.

Particulate solids, especially beads are preferred for use in the methods of the invention. Monodisperse particles, that is those which are substantially uniform in size (e.g. having a diameter standard deviation of less than 5%) have the advantage that they provide very uniform reproducibility of reaction.

When the solid is particulate, for example a bead, a force between the recognition agent and the cell is preferably introduced by perturbing a liquid medium containing the particle. This embodiment will be further described with reference to beads wherein the beads need to be of a size and density such that the force set up between the recognition agent and the cell during perturbation of the liquid medium is sufficient to, for example, separate the cell and the bound recognition pair complex. The density of the bead is preferably 1.3–2.8 g/ml, more preferably 1.4–2.4 g/ml, most preferably 1.4–2.1 g/ml. The bead preferably has a diameter less than the diameter of the cell, more preferably a diameter of less than a third the diameter of the cell and most preferably a diameter of 3–4.5 $\mu$m. The type of bead is not particularly limited, provided that it does not adversely affect transfection. The bead is preferably a magnetic or magnetisable bead, or a silica bead.

When the bead is a magnetic or magnetisable bead, any type of magnetic separation can be used. Preferably the beads are first added to the liquid medium containing the cells. The beads are then simply allowed to settle onto a monolayer of cells, and then, after an appropriate period of time (e.g. up to 30 mins) allowing for attachment of the beads to the cells, a magnet is brought into proximity with the liquid medium (e.g. by placing the magnet on top of the tissue culture bottle—the size of the bottle is not particularly limited, provided that the magnet can be brought close enough to the beads to apply sufficient force to the beads) to remove the beads from the cells. In this embodiment, there is no requirement to perturb the liquid medium, since the magnet exerts a force on the magnetic or magnetisable beads pulling them away from the cells. Typically, cell containers can be placed under a magnet for 3–20 minutes, allowing the beads to be pulled away from the cells, thereby creating holes and allowing the substance which it is intended to introduce into the cells to diffuse into the cells.

There is no particular limitation on the ratio of beads to cells used in the present method, but ratios of less than 50:1 are preferred. When the cells are suspension cells, the preferred ratio of beads/cells is any ratio up to 20:1. When the cells are adherent cells, the preferred ratio of beads/cells is any ratio up to 10:1.

In the case where the liquid medium is perturbed, perturbation preferably comprises centrifugation and/or mixing, e.g. mixing by stirring or end-over-end mixing. Perturbation may also include agitation of the liquid in any other manner, provided that sufficient force is set up between the recognition pair complex and the cell to separate the bound recognition pair complex from the cell. Without being bound by theory, it is believed that the perturbation may set up shear forces which separate the bound recognition pair complex from the cell, or forces acting along the axis of bonding between the cell and the recognition agent which separate the bound recognition pair complex from the cell.

When the solid is other than a particulate solid such as a bead, it is preferred that, once the cells are attached to the recognition agents, a liquid medium is allowed to flow across the surface of the solid. Without being bound by theory, it is thought that in this embodiment shear forces are set up which separate the cell from the bound recognition pair complex. In this embodiment the cells are preferably captured on the surface of a test tube or a well and the surface is then washed with a liquid medium. Preferably, the cells are removed from the solid surface by washing them with a fast stream of saline solution containing the substance to be introduced into the cell.

In an alternative embodiment, the recognition agent which binds to the recognition site may not be bound to a solid but may bind to a further agent which is itself bound to a solid. For example, beads may be provided coated with a secondary antibody together with a selection of primary antibodies (recognition agents) targeted to different recognition sites, possibly to different types of cells, all of which primary antibodies bind to the secondary antibody on the beads. Alternatively the recognition agent may be a fusion molecule allowing affinity binding to the further intermediate agent, to allow e.g. streptavidin:biotin binding. In general binding of a recognition agent to a solid support via the intermediacy of one or more further molecules may be achieved using affinity binding or e.g. covalent, hydrophobic or ionic binding. It will be appreciated however that for performance of the invention the association between the recognition agent and the intermediate binding molecule is necessarily stronger than between the recognition agent and the recognition site.

In all of the embodiments employing a liquid medium, it is preferred that the substance to be introduced into the cell is contained within the liquid medium. In this preferred embodiment the substance is introduced into the cell in a step which is simultaneous with the step of separating the recognition agent from the cell. However, it is also possible that the substance can be contacted with the cells once they have been removed from the recognition agent and the transient holes have been created in the cell surface, provided that the substance is introduced before the transient holes in the cell surface re-seal.

Achievement of appropriate separation of the recognition agent from the cell (e.g. by peturbation) may be conveniently assessed by monitoring the extent of transfection, i.e. the number of cells into which the substance to be transfected (e.g. a test molecule) is introduced. Preferably at least 65% of cells, e.g. 75%, more preferably 80% are transfected.

The liquid medium employed is not particularly limited and is preferably an aqueous medium. The medium may be a buffer or a cell culture medium. The concentration of the substance in the medium is not particularly limited and may be selected according to the quantity of substance which is required to be introduced into the cell. As discussed previously, transfection may be optimised by selection of a particular osmolarity for the liquid medium, taking into consideration the osmolarity of the cells to be transfected and whether the cells are adherent or in suspension.

The substance to be introduced can be any substance and will preferably not be endogenous to the cell into which it is to be introduced. Preferably the substance is a substance not normally able to cross the cell membrane. It is preferred that the substance to be introduced into the cell is a hydrophilic substance, however the substance may also be hydrophobic. Any biological molecule or any macromolecule e.g. a complex of molecules can be introduced into the cell. The substance generally has a molecular weight of 100 daltons or more. In a more preferred embodiment, the substance is a nucleic acid molecular such as DNA, RNA, PNA (e.g. cDNA, genomic DNA, a plasmid, a chromosome, an oligonucleotide, a nucleotide sequence, or a ribozyme) or a chimeric molecule or a fragment thereof, or an expression vector. Additionally, the substance may be any bio-active molecule such as a protein, a polypeptide, a peptide, an amino acid, a hormone, a polysaccharide, a dye, or a pharmaceutical agent such as drug. Conveniently the substance to be introduced is present in the liquid medium at a concentration of 0.2 to $10 \times 10^{-8}$ M, e.g. $0.75-1.25 \times 10^{-8}$ M.

The cells to which the method of the present invention can be applied are not particularly limited and induce prokaryotic and eukaryotic cells, preferably mammalin e.g. human, cells. It is preferred that the cell against which the method is employed is an animal cell. However, the method can also be employed to treat cells with cell walls, such as plant cells, fungal cells and bacteria. In this latter embodiment, it is preferred that the method is carried out on a protoplast derived from the cell which has had its cell wall partially or completely removed.

Using the method of the present invention, a population of cells can be transfected. These cells may, for instance, be in the form of a cell suspension or may be adherent cells on a solid surface. Suitable solid surfaces include all those discussed previously in connection with the solid to which the recognition agent is attached. Here, however, the solid surface will preferably be a slide, well, dish, flask, plate etc., made conveniently from glass or plastic. The method may also be employed to treat a cell population containing a plurality of cell types. The recognition agent may be specific to a recognition site present on the surface of one or more target cell types in the population, such that the substance is selectively introduced into target cell types within the population.

Thus, in a preferred embodiment of the present invention is provided a method for introducing a non-endogenous nucleic acid molecule into a cell, which method comprises contacting the cell with an antibody attached to a bead, said antibody being able to bind to an antigen on the surface of the cell. When the bead is magnetic or magnetisable, the antibody-coated beads are removed from the cell by introduction of a magnet which attracts the beads away from the cells causing sufficient force to form holes in the cells and thus influx of nucleic acid molecules. When the beads are not magnetic or magnetisable or the magnetic or magnetisable properties of the beads are not to be used in the separation, the liquid medium which contains the cells, nucleic acid material to be introduced and the antibody-coated beads is perturbed by centrifugation or end-over-end mixing to cause separation of the antibody from the cell, hole formation and introduction of the nucleic acid molecule.

The present invention also provides a kit for introducing a substance into a cell, which kit comprises;

(i) a solid surface for attaching to a recognition agent;

(ii) a liquid medium having an osmolarity of from 30–1200 mOsm;

(iii) optionally a recognition agent capable of binding to a recognition site on the surface of a cell to form a recognition pair; and (iv) optionally, a means for attaching the recognition agent to the solid surface.

The solid surface is not particularly limited, provided that it is suitable for recognition agents to be attached to, and convenient examples have been discussed herein.

In one embodiment in which the kit is suitable for transfecting adherent cells, the osmolarity of the liquid medium provided with the kit is from 20–150, e.g. 40–100 mOsm, more preferably from 40–50 mOsm. In an alternative embodiment in which the kit is suitable for transfecting suspension cells, the osmolarity of the liquid medium provided with the kit is from 800–1000 mOsm, more preferably from 950–1000 mOsm.

The recognition agent can be attached to the solid surface by any means, either direct or indirect, including adsorption onto the surface, covalent linking to the surface, attachment through a nucleic acid linker, or attachment through a linker that is capable of being cleaved chemically or enzymatically. Preferably, the means for attaching the recognition agent to the solid surface is a biotin/avidin coupling, a biotin/streptavidin coupling, or a biotin/modified avidin coupling. The solid surface is preferably coated with avidin and then reacted with a biotinylated antibody. The solid surface is preferably one or more beads.

When the recognition agent is an antibody, the kit may contain a secondary antibody specific to a range of primary antibodies. The kit may thus further contain one or more primary antibodies specific to one or more antigen on the surface of a cell. When a secondary antibody is employed, the secondary antibody is preferably biotinylated to attach it to avidin coated beads. In one variation of the present invention, primary antibodies may first be attached to the cells and then removed by mixing them with beads coated with the secondary antibody. In a further variation, both primary and secondary biotinylated antibodies can be bound to the cells and then mixed with avidin coated beads.

Furthermore, the solid surface may be coated with more than one type of recognition agent to allow the simultaneous transfection of more than one type of cell.

A further example of a kit provided by the invention for introducing a substance into a cell comprises:

(i) a recognition agent capable of binding directly or indirectly to a recognition site on the surface of the cell, said recognition agent optionally being attached to a solid surface;

(ii) optionally a liquid washing medium; and (iii) optionally a liquid immunoporation medium.

The washing medium, is preferably aqueous and may be a buffer or cell culture medium, preferably an isotonic saline medium of physiologically acceptable pH. The immunoporation medium is a liquid medium as previously defined, e.g. a salt solution which may contain nutrient factors, it will have an osmolarity selected to optimise the introduction of the substrate into the cell in the manner previously discussed. The immunoporation medium in the kit may contain the substance to be introduced into the cell but more preferably this will be added to the immunoporation medium by the person using the kit.

Indirect binding as referred to in part (i) above refers to the situation, for example when the recognition agent is an antibody, that the recognition agent which is bound to a solid surface binds to a factor, e.g. to another antibody which itself binds to the recognition site, e.g. antigen, on the surface of the cell.

When carrying out the method of the present invention, mixing is preferably employed to perturb a liquid medium containing the cell/recognition agent complex. Mixing preferably takes place for a period of from 2–15 hours, more preferably 2–5 hours, most preferably around 3 hours depending on the exact nature of the cell and result required. Longer mixing times may give the best results with certain cell types, for example Human Daudi B cells, originally derived from a patient with Burkitt's lymphoma, maximum levels of transfection when the cells were mixed with antibody-coated beads for 12–18 hours. Optimal mixing times will depend on the nature of the recognition site and its interaction with the cell membrane and other cellular components, particularly the cytoskeleton.

When an antibody is employed as recognition agent, the antibody used is preferably specific to a protein antigen on the surface of the cells. Alternatively, the antibodies may be specific to other antigen types on the cell surface, such as polysaccharides.

The present invention also provides use of a recognition agent capable of binding to a recognition site on the surface of a cell, in the introduction of a substance into the cell.

The method, kits and use of the present invention can be used in non-medical applications, such as in life-sciences applications, as well as in medical applications.

Life sciences applications in which the present invention can be particularly useful include the introduction of specific genes into viable cells for expression and for the analysis of the effect of gene products on the metabolism of cells. Appropriately transfected cells may also be used to express useful products which may be harvested, e.g. human insulin. Such applications also include the introduction of biologically active proteins into viable cells to study their effects on the cells with regard to the metabolism and morphology of the cells. These applications also extend to the introduction of pharmacologically important compounds into cells, where the cell membrane is normally impervious to such compounds. Cells transfected according to the method described herein form a further aspect of the invention.

Medical applications in which the present invention can be particularly useful include all applications which are not life sciences applications as defined above, and specifically include gene therapy and the targeted introduction of new genes into specific immunologically defined cell populations with deleted or defective genes. Such applications also include the introduction of genes controlling endocrine functions, such as hormone synthesis and secretion, into epidermal cell populations. The targeted permeabilisation of tumour cells for enhanced chemotherapy procedure is also included in these applications. In particular, the method kit and use of the present invention may be employed in gene therapy to great advantage. For example, they may be used in the treatment of leukaemic cells, such cells being treated in suspension in preference to non-leukaemic cells present in the same suspension. Additionally, the invention may be used to introduce antisense RNA into specific cell types. The method may be used ex vivo, on cells in body fluids, tissue or organs, which may be reintroduced into the body, or in vivo In comparison to known methods, the present method is very efficient. The efficiency i.e. the proportion of cells into which the target substance has been introduced, depends, inter alia, on the length of time during which mixing is carried out and the vigorousness of the mixing. Efficiency of at least 70%, preferably at least 80%, more preferably at least 90% can be achieved and in some circumstances, an efficiency of 100% can be approached. In embodiments where there is no mixing as such, e.g. where the cells are adherent and separation occurs as a result of magnets pulling magnetic or magnetisable beads away from the cells, efficiencies of at least 85%, preferably 90% or more can readily be achieved.

The invention will now be further described, by way of example only, with reference to the following specific embodiments.

EXAMPLES

Cells

Daudi B cells were cultured in RPMI 1640 medium (Imperial Labs, Andover, UK) containing 10% foetal calf serum (FCS) (Gibco, BRL, USA). For bead binding experiments, cells were harvested from the culture and centrifuged over a cushion of 0.5 ml isotonic Nycodenz to pellet non-viable cells. Cell viability was tested using Trypan blue.

HL60 cells were cultured in RPMI 1640 medium (Imperial Laboratories, Andover, UK) containing 10% FCS. For bead binding experiments, cells were harvested from the culture and centrifuged over a cushion of 0.5 ml isotonic Nycodenz to pellet non-viable cells. Cell viability was tested using Trypan blue.

HeLa cells were cultured in DMEM medium (Life Science International, UK) containing 10% FCS.

D532 cells were cultured in DMEM medium containing 10% FCS.

Example 1

Silica Beads

Coating Beads with Antibody

Avidin coated 100-3 Nucleosil silica beads (Macherey-Nagel) were incubated with biotinylated rabbit anti-mouse secondary antibody by mixing $5 \times 10^7$ beads with 5.5 µg of the antibody in a final volume of 125 µl Earl's balanced salt solution (EBSS) containing 10% donor calf serum (DCS). This suspension was allowed to mix on an end-over-end mixer (Robbins Scientific Corp., USA) rotating at 15 rpm for 45 min at room temperature. After binding, the beads were pelleted and washed three times with 10% (w/v) DCS in EBSS. The beads were then re-suspended in EBSS.

The primary antibody was added to either $5 \times 10^7$ silica beads coated with secondary antibody, or the same number of Dynabeads® M-450 coated with sheep anti-mouse IgG. The primary antibody, mouse anti-human CD19, was used to target beads to the cell surface antigen CD19 that is highly expressed in Daudi cells. All sets of beads were allowed to bind to the primary antibody (0.8 µg) by incubation on the end-over-end mixer for 60 min at room temperature. The labelled beads were washed three times with 10% (w/v) DCS in EBSS. For control purposes, beads were coated with biotinylated secondary antibody and alternative monoclonal antibody not specific for any of the cell surface antigens, as described previously.

Transfection of Proteins into the Cells

The cells ($2.5 \times 10^6$) were suspended in 1 ml EBSS containing 10% DCS and incubated whilst mixing together with the washed, antibody-coated beads and in the presence of fluorescently labelled proteins (either FITC-labelled BSA or cytochrome-c) in a screw-cap 1.5 ml microcentrifuge tube. Incubation took place over a 12 hr period at room temperature on the end-over-end mixer. The ratio of beads to cells was 40:1. The concentrations of fluorescently labelled proteins used for this experiment were varied over a range of $1-15 \times 10^{-8}$ M. A similar incubation of cells, in the presence of the non-specific antibody-coated beads was used as a control.

The separation of cells and bead-bound cells from the beads was achieved using isopycnic density gradient centrifugation. Cells in the incubation medium were layered on to 1.5 ml of a solution of isotonic Optiprep (1.32 g/ml) and centrifuged for 20 min at 270×g at 20° C. Cells harvested from the interface were transferred to another tube and washed three times in phosphate buffered saline (PBS) and re-suspended in EBSS. Samples were checked under a fluorescence microscope for viability and for fluorescence.

The viability of the cells was found to be 75%. Furthermore, only those cells that had been mixed with beads with bound antibody against CD19 were found to be fluorescent.

Example 2

Magnetisable Beads

Coating Beads with Antibody

M-450 Dynabeads® were coated with 1.5 µg of antibody per $1 \times 10^7$ beads to achieve maximum coating of the beads. One aliquot (100 µl) of SAM (sheep anti-mouse) M-450 beads were transferred to a microcentrifuge tube containing 800 µl EBSS/10% FCS. The liquid was placed in a Dynal® magnetic separator and aspirated. The beads were then washed twice with 1.0 ml EBSS/10% FCS. After the final wash 400 µl EBSS/10% FCS were added. The following antibodies were then added to separate quantities of the beads:

W6/32 (0.5 mg/ml stock 12 µl (6 µg); solution)

Anti-CD71 (175 mg/ml stock 3.4 µl of a 1/100 solution) dilution (6 µg);

Anti-CD11b (100 µg/ml stock 60 µl (6 µg) solution).

The beads were incubated with the antibody for 1 hr at room temperature (20° C.) on an end-over-end mixer rotating at 33 rpm. The beads were then washed three times with 1.0 ml EBSS/10% FCS. After the final wash 100 µl EBSS/10% FCS were added. If the beads are to be stored, sodium azide can be added to a concentration of 0.02%.

Calculation of the amount of transfection agent It is important to determine the required concentration of the agent that is to be transfected into the cell. Macromolecules enter cells by an osmotically enhanced diffusion process and typical concentrations used are from $0.2-10 \times 10^{-8}$ M. Whilst it is not usually necessary to know the exact concentration, the concentration is preferably controlled within a range which is not excessively concentrated or dilute, so that the correct quantity of substance is transfected into the cell.

A useful relationship in determining concentration is that the molecular weight of any molecule expressed in µg/ml corresponds to a $1 \times 10^{-3}$ M concentration. For instance, it can be assumed when calculating the molecular weight of DNA, that the molecular weight of a base pair is 600. Hence a 5 kb DNA vector has a molecular weight of $3 \times 10^6$ and so a solution of 30 mg/ml of this vector has a concentration of $1 \times 10^{-8}$ M.

Immunoporation of Adherent Cells

The cells to be immunoporated are preferably spread apart to allow a greater surface area of cells to be exposed. Thus, with HeLa cells for example, it is better to passage them to the required density up to a day prior to treatment. On the other hand, some cells, such as D 532 cells, are usually very well spread and prior passaging is not necessary.

If the cells are to be analysed by confocal microscopy, they are preferably grown and transfected on either a LabTek® slide or in a Flaskette®, both of which facilitate direct microscopy of live cells immediately after transfection. Cells grown on glass do not adhere as strongly as cells grown on plastic, and so greater care must be taken when washing cells in the Flaskette®. When using the LabTek®, it is important not to vacuum aspirate, but to use an automated pipette.

In the present Example, the following steps were carried out to transfect the adherent cells, all steps being carried out under sterile conditions.

HeLa and D532 cells to be immunoporated were counted. A volume of EBSS (determined from Table 1 below) was added to three separate test tubes. The antibody-labelled beads were then added to the test tubes at a ratio of 10 beads per cell (if the beads have been stored in the presence of azide, the azide must first be washed away). Having calculated the amount of substance (in this Example DNA, protein and dextran) with which to transfect $2 \times 10^6$ cells, 30 µg, of pEGFP-C1 vector, 2.5 µg of fluorescently labelled bovine serum albumin FITC-BSA and 2.5 µg of Rhodamine-Dextran were added to separate test tubes containing the beads and the transfection medium.

The cells were then washed twice in their respective containers, with pure transfection washing medium (medium not containing beads or macromolecules). The volumes employed for each container were as follows:

TABLE 1

| Transfection container | Volume |
| --- | --- |
| Each well of a LabTek | 350 µl |
| 25 cm² tissue culture flask | 5.0 ml |
| Slide flaskette | 3.0 ml |
| Petri dish 35 mm | 2.0 ml |
| 60 mm | 4.0 ml |
| 90 mm | 12.0 ml |

The transfection medium, beads and macromolecules were then mixed and then the medium containing either DNA, protein or dextran was added to the cells in a volume suitable for the transfection container, as shown above. The beads were allowed to bind to the cells for 10 mins with occasional gentle mixing movements of the containers.

The cell containers were then placed under a magnet and left for 10 mins, allowing the beads to be pulled up from off the cells, thereby allowing the transfection macromolecules to diffuse into the cells. The containers were then removed from under the magnet and then placed under the magnet again. This procedure was repeated a further two times.

After the final time under the magnet, the containers were slid under the magnet so as to move the beads to the side of the container. The immunoporation transfection medium was then removed by aspiration. The cells were washed three times with 5 ml transfection washing medium, each time placing the containers under the magnet to lift the beads from the cells and sides of the containers. After the final wash, the cells were checked under a microscope to ensure that no further beads were remaining. Further washing was carried out to remove the remaining beads if necessary.

Normal growth medium was then added to the cells, and then the cells were returned to an incubator. Cells transfected with protein or dextran could be analysed after 1 hr, either by flow cytometry or confocal microscopy. Cells transfected with DNA were cultured for a further 24–28 hrs for the GFP (green fluorescent protein) to be expressed in sufficient quantity to be detectable.

Analysis of Transfected Adherent Cells (i) Confocal Microscopy This operation needs to be performed using as little illumination as possible, to prevent photo-bleaching.

The transfected cells were washed twice with transfection washing medium. The flask or chamber was removed from the slide, the cells were covered with a minimum quantity of transfection washing medium, a coverslip was placed over the cells and the coverslip was sealed with grease.

The analysis was performed under a microscope according to standard confocal microscopy techniques. Both HeLa cells and D532 cells transfected with DNA, protein or dextran exhibited clear fluorescence present inside the cells, not at the cell surface. Thus both types of cell were successfully transfected with all three types of molecule. In each case approximately 90% or more transfection was achieved, with cell death being approximately 20% or less.

(ii) Flow Cytometry This operation must also be carried out using as little illumination as possible to prevent photo-bleaching. At least 40,000 cells are required for this procedure, an optimum number is 100,000–200,000. A sample of untransfected cells is also required for comparison.

The transfected cells were washed with 0.2 µl of filtered PBS (phosphate buffered saline). The cells were then incubated with a minimum quantity of trypsin-EDTA (TE) (1 ml in a 25 ml flask) and returned to the incubator for 5 mins. The flask was knocked to dislodge the cells—a microscope was used to ensure that the cells had lifted from the flask surface. Normal incubation medium was added (4×TE volume) to neutralise the trypsin.

The cells were centrifuged (1200 g, 5 mins) and washed three times with PBS (1 ml) using a microcentrifuge. After the final wash the cells were re-suspended in 100 µl PBS. Analysis was carried out using standard flow cytometry methods. Cells transfected with DNA showed a clear increase in peal channel and mean over control cells, indicating that they were fluorescent and had thus been transfected.

Immunoporation of Suspension Cells

As in the above examples, all of the steps in the following example were carried out under sterile conditions.

Daudi B cells and HL60 cells to be transfected were counted and transferred to microcentrifuge tubes in aliquots of 200,000. The cells were washed twice with transfection washing medium using a microcentrifuge set at low speed.

The final pellets were re-suspended in 500 µl transfection washing medium and the antibody-labelled beads were added to the transfection medium at a ratio of about 20 beads per cell. Having calculated the amount of substance (DNA, protein or dextran) with which the cells are to be transfected, either 6 µg of pEGFP-C1 vector, 2.5 µg of FITC-BSA or 2.5 µg Rhodamine-Dextran were added to the transfection medium.

The cells, beads and macromolecules were then incubated in the transfection medium on an end-over-end mixer operating at 33 rpm, for 3 hrs at room temperature.

Bead-free cells were recovered using a magnetic separator; the beads adhere to the magnet and the cells present in the supernatent are removed. The cells were washed within the supernatent three times, each time with 1 ml of transfection washing medium using a microcentrifuge set at low speed. If beads are still present in the pellet, the cells can be re-suspended and placed on the magnetic separator again The cells are then re-suspended in normal growth medium and returned to the incubator. Cells transfected with protein or dextran could be analysed after 1 hr, either by flow cytometry or confocal microscopy. Cells transfected with DNA were cultured for a further 24–28 hrs for the GFP (green fluorescent protein) to be expressed in sufficient quantity to be detectable.

Analysis of Transfected Suspension Cells (i) Confocal Microscopy This operation needs to be performed using as little illumination as possible, to prevent photo-bleaching.

The transfected cells were washed twice with PBS. The cells (approx. 1×10$^4$ in number) were re-suspended in 20 µl PBS and placed in the wells of a poly-L-lysine coated microscope slide. The cells were then allowed to settle for 20 mins.

The PBS was then gently removed and PFA (paraformaldehyde) was added (4%, 20 µl). The cells were left to be fixed for 20 mins. Then, the PFA was gently removed and 15 µl of DABCO (1,4-diazabicyclo-[2,2,2] octane) was added. A coverslip was placed over the cells and sealed with grease.

The analysis was performed under a microscope according to standard confocal microscopy techniques. Both Daudi B cells and HL 60 cells transfected with DNA, protein or dextran exhibited clear fluorescence present inside the cells, not at the cell surface. Thus both types of cell were successfully transfected with all three types of molecule. In each case approximately 80% or more transfection was achieved, with cell death being approximately 20% or less.

(ii) Flow Cytometry This operation must also be carried out using as little illumination as possible to prevent photobleaching. At least 40,000 cells are required for this procedure, an optimum number is 100,000–200,000. A sample of un-transfected cells is also required for comparison.

The transfected cells were washed with 0.2 µl of filtered PBS using a microcentrifuge set at low speed. After the final wash the cells were re-suspended in 100 µl PBS. Analysis was carried out using standard flow cytometry methods. Cells transfected with DNA showed a clear increase in peal channel and mean over control cells, indicating that they were fluorescent and had thus been transfected.

Example 3

Effect of Osmolarity on Transfection

HL60 suspension cells were transfected as described in Example 2. The osmolarity of the transfection (immunoporation) medium was varied to determine its effect on the transfection efficiency and transfection rate.

Eight different transfection media having osmolarities from 250 mOsm–1000 mOsm were made up using EBSS of varying salt content. These media were used to transfect HL60 cells in the presence and absence of DCS. The effect of the osmolarity of the transfection medium on the percentage of cells transfected is depicted in FIG. 1.

It is clear from FIG. 1 that the most efficient transfection is observed for suspension cells when the osmolarity of the transfection medium is from 700 mOsm–1000 mOsm.

As can be seen from FIG. 1, the presence of serum inhibits transfection and thus preferably the methods of the invention will be performed in a liquid environment which lacks serum, e.g. non-human animal serum. Thus the liquid (transfection/immunoporation) medium, will preferably not contain or comprise serum.

Example 4

Methods

HL-60 cells were cultured in RPMI 1640 medium containing 10% FCS, and differentiated by the addition of 1.25% DMSO. Prior to transfection, cells were washed twice with washing medium (Dynal AS) and resuspended at a concentration of $4 \times 10^5$ ml$^{-1}$ in 0.5 ml of immunoporation transfection media (Dynal AS). Dynaf ect beads (Dynal AS) were added to the cells at a ratio of 20:1. The transfection agent, either tetramethyl-rhodamine dextran (70 Kda) (0.25 µg) (Molecular Probes) or FITC BSA (0.25 µg) or the green fluorescent protein(GFP) encoding vector pEGFP-C1 (3 µg) (Clontech), was then added to the cells and the cells were mixed on an end-over-end mixer at 33 rpm at room temperature (22° C.). The Dynafect beads were then separated from the cells on a magnetic separator (Dynal AS), and the cells washed three times with immunoporation washing media (Dynal AS). After washing, those cells transfected with tetramethyl-rhodamine dextran (TMR-dextran) were immediately analysed by confocal microscopy (BioRad). Those cells transfected with the GFP-encoding vector pEGFP-C1 were resuspended in RPMI containing 10% FCS and cultured for a further 48 hours, after which time they were analysed by flow cytometry (Becton Dickinson). Control Dynafect beads (Dynal AS) were prepared in the absence of specific antibody and shown not to bind to the cell surface of HL-60 cells.

HL-60 cells, which are derived from human leukaemic cells, normally express the transferrin receptor, CD71, on their surface. When induced to differentiate in the presence of DMSO, the resulting granulocytes cease to express CD71 and instead express high levels of CD11b. We have used the varying antigen expression of this cell line as a model system to investigate the process of cell transfection mediated by antibody-coated beads. Dynafect beads (Dynal AS, Norway) coated with either anti-CD11b antibody or anti-CD71 antibody were mixed on an end-over-end mixer at 33 rpm for 3 hours at room temperature (22° C.) with either uninduced HL-60 cells or cells that had been induced with DMSO for 3 days. The cells and beads were resuspended in a proprietary transfection medium (Dynal AS) in the presence of tetramethyl-rhodamine dextran (TMR-dextran) (mol. wt 70 Kda). After mixing, the transfected cells were washed, and analysed by confocal microscopy. The confocal images (FIG. 2) show that uninduced HL-60 cells were only transfected with TMR-dextran when incubated with anti-CD71 Dynafect beads, CD71 being the antigen expressed on normal HL-60 cells. In contrast, the HL-60 cells induced to differentiate by growth in DMSO for three days were only transfected with TMR-dextran in the presence of anti-CD11b coated Dynafect beads, CD11b being the antigen expressed on differentiated HL-60 cells. Three-dimensional, confocal imaging of the cells confirmed that the TMR-dextran was incorporated into the cytoplasm of the cell and was not simply bound to the cell membrane. Experiments carried out using FITC labelled bovine serum albumin (FITC-BSA) gave very similar patterns of transfection.

Using exactly the same mixing procedure, HL-60 cells were also transfected with the plasmid DNA vector pEGFP-C1 (4.76 kb, mol. wt $2.8 \times 10^6$) that codes for green fluorescent protein (GFP). After transfection the cells were transfected back into tissue culture medium and cultured for a further 48 hours before analysis. In this case, in order to obtain a more quantitative determination of transfection, the extent of cell transfection was determined by flow cytomeric analysis. From FIG. 3 we can see that the anti-CD71 coated Dynafect beads facilitate the transfection of DNA into normal HL-60 cells, which express CD71, but when the cells become differentiated and no longer express CD71, transfection does not occur with these beads. In contrast, mixing the cells with the anti-CD11b coated Dynafect beads does not result in the transfection of normal HL-60 cells with DNA, but when the cells are differentiated and begin to express CD11b, those beads do bring about transfection. Hence, immunoporation has the potential to target specific types of cells in a mixed population for transfection depending on their immunological identity, and allow the targeted cells to take up a variety of different types of molecules.

What is claimed is:

1. A method for introducing a substance into a cell, which method comprises;
    (a) contacting the cell with a recognition agent to bind the recognition agent to a recognition site on the surface of the cell;
    (b) separating the recognition agent from the cell thereby forming a hole in the surface of the cell; and
    (c) introducing the substance into the cell.

2. A method according to claim 1, wherein step (b) is carried out in a liquid medium.

3. A method according to claim 1, wherein the recognition agent is attached to the surface of a solid prior to contacting it with the cell.

4. A method according to claim 1, wherein the substance comprises at least one material selected from the group consisting of bio-active molecules, DNA, RNA, PNA, genes, plasmids, chromosomes, oligonucleotides, nucleotide sequences, ribozymes, expression vectors, proteins, polypeptides, peptides, amino acids, hormones, polysaccharides, dyes, pharmaceutical agents, and fragments of any of the foregoing.

5. A method according to claim 1, wherein the cell is an animal cell.

6. A method according to claim 1, wherein the cell is a protolast derived from a cell having a cell wall.

7. A method according to claim 1, wherein the cell is a member of a population of cells.

8. A method according to claim 1, wherein the recognition agent is selected from the group consisting of antibodies, antigens, growth factors, growth factor receptors, sugars, sugar receptors, hormones, hormone receptors, cell adhesion molecules, enzymes, enzyme substrates, co-enzymes, proteins, synthetic ligands, synthetic receptors, phages, phage receptors and molecules capable of binding with any of the foregoing.

9. A method according to claim 2, wherein the osmolarity of the liquid medium is from 0.1 to 4.0 times the osmolarity of the cell.

10. A method according to claim 2, wherein the osmolarity of the liquid medium is, from 30 to 1200 mOsm.

11. A method according to claim 2, wherein step (b) comprises perturbing the liquid medium.

12. A method according to claim 2, wherein the liquid medium comprises the substance to be introduced.

13. A method according to claim 3, wherein the solid is a particulate.

14. A method according to claim 3, wherein the solid is a bead.

15. A method according to claim 3, wherein the solid is a bead, which bead has a density of 1.3 to 2.8 g/ml.

16. A method according to claim 3, wherein the solid is a bead with a diameter less than the diameter of the cell.

17. A method according to claim 3, wherein the bead has a diameter of from 3 to 4.5 micrometers.

18. A method according to claim 3, wherein the solid is a bead selected from the group consisting of silica beads, magnetic beads, and magnetizable beads.

19. A method according to claim 3, wherein the solid is non-particulate.

20. A method according to any one of claims 2, 9, 10, or 12, wherein step (b) comprises perturbing the liquid medium.

21. A method according to any one of claims 2, 9, 10, or 12 comprising allowing the liquid medium to flow across the surface of the cell.

22. A method according to any one of claims 2, 9, 10, or 12, wherein the recognition agent is selected from the group consisting of antibodies, antigens, growth factors, growth factor receptors, cell adhesion molecules, enzymes, enzyme substrates, co-enzymes, proteins, synthetic ligands, synthetic receptors, phages, phage receptors, and molecules capable of binding to any of the foregoing.

23. A method according to any one of claims 2, 9, 10, or 12, wherein the substance comprises at least one material selected from the group consisting of bioactive molecules, DNA, RNA, PNA, genes, plasmids, chromosomes, oligonucleotides, nucleotide sequences, ribozymes, expression vectors, proteins, polypeptides, peptides, amino acids, polysaccharides, dyes, pharmaceutical agents, and fragments of any of the foregoing.

24. A method according to any one of claims 3, 14, 15, 16, 17, 18, or 19, wherein step (b) comprises at least one process selected from the group consisting of perturbing the liquid medium, centrifugation, end-over-end mixing, contact with a magnetic field, and causing the liquid medium to flow across the surface of the solid.

25. A method according to claim 7, wherein the population of cells is selected from the group consisting of a cell suspension and an adherent cell population.

26. A method according to claim 7, wherein step (b) is carried out in a liquid medium and wherein the osmolarity of the liquid medium is from 800 to 1200 mOsm.

27. A method according to claim 7, wherein step (b) is carried out in a liquid medium and wherein the osmolarity of the liquid medium is from 30 to 150 mOsm.

28. A method according to claim 7, wherein the population contains a plurality of cell types and the recognition agent is specific to a recognition site present on the surface of one or more, but less than all, cell types, in the population, such that the substance is selectively introduced into selected cell-types within the population and wherein step (b) is carried out in a liquid medium.

29. A method according to claim 28, wherein the osmolarity of the liquid medium is from 800 to 1200 mOsm.

30. A method according to claim 28, wherein the osmolarity of the liquid medium is from 30 to 150 mOsm.

31. A method according to claim 28, wherein the recognition agent is selected from the group consisting of antibodies, antigens, growth factors, growth factor receptors, sugars, sugar receptors, hormones, hormone receptors, cell adhesion molecules, enzymes, enzyme substrates, co-enzymes, proteins, synthetic ligands, synthetic receptors, phages, phage receptors, and molecules capable of binding with any of the foregoing.

32. A method according to claim 28, wherein the substance comprises at least one material selected from the group consisting of bioactive molecules, DNA, RNA, PNA, genes, plasmids, chromosomes, oligonucleotides, nucleotide sequences, ribozymes, expression vectors, proteins, polypeptides, peptides, amino acids, hormones, polysaccharides, dyes, pharmaceutical agents, and fragments of any of the foregoing.

33. A method according to claim 28, wherein the recognition agent is attached to the surface of a solid prior to contacting it with a cell.

34. A method according to claim 33, wherein the solid is a particulate.

35. A method according to claim 33, wherein the solid is a bead.

36. A method according to claim 33, wherein the solid is a bead selected from the group consisting of silica beads, magnetic beads, and magnetizable beads.

37. A method according to any one of the claims 28, 29, 30, 31, 32, 33, 34, 35, or 36, wherein step (b) comprises at least one process selected from the group consisting of perturbing the liquid, medium, centrifugation, end-over-end mixing, contact with a magnetic field, and causing the liquid medium to flow across the surface of the solid.

38. A method according to claim 37, wherein the population of cells is selected from the group consisting of a suspension of cells and a population of adherent cells.

39. A method according to any one of claims 3, 13, 14, 15, 16, 17, 18, 19, 33, 34, 35, or 36, wherein the means for attaching the recognition agent to the solid surface is selected from the group consisting of:
   (i) a biotin/avidin coupling;
   (ii) a biotin/streptavidin coupling;
   (iii) a biotin/modified avidin coupling;
   (iv) adsorption onto the bead surface;
   (v) covalent linking to the bead surface;
   (vi) attachment through a nucleic acid linker; and
   (vii) attachment through a linker which can be cleaved chemically or enzymatically.

40. A kit for introducing a substance into a cell according to the method of any one of claims 1, 2, or 3–19, which kit comprises:
   (i) a recognition agent capable of binding directly or indirectly to a recognition site on the surface of the cell, said recognition agent optionally being attached to a solid;
   (ii) optionally, a liquid washing medium; and
   (iii) optionally, a liquid immunoporation medium.

41. A kit for introducing a substance into a cell, which kit comprises;
   (i) a solid surface for attaching to a recognition agent;
   (ii) a non-isotonic liquid medium;
   (iii) a recognition agent capable of binding to a recognition site on the surface of a cell to form a recognition pair; and
   (iv) optionally, a means for attaching the recognition agent to the solid surface.

42. A kit according to claim 41, wherein the recognition agent is an antibody.

43. A kit according to claim 42, wherein the antibody is a secondary antibody specific to a range of primary antibodies.

44. A kit according to claim 43, which further comprises a primary antibody specific to an antigen on the surface of a cell.

45. A kit according to any one of claims 41, 42, 43 or 44, wherein the means for attaching the recognition agent to the solid surface is selected from the group consisting of:
   (i) a biotin/avidin coupling;
   (ii) a biotin/streptavidin coupling;
   (iii) a biotin/modified avidin coupling;
   (iv) adsorption onto the bead surface;
   (v) covalent linking to the bead surface;
   (vi) attachment through a nucleic acid linker; and
   (vii) attachment through a linker which can be cleaved chemically or enzymatically.

46. A process for the introduction of a substance into a cell, said process comprising contacting the cell with a recognition agent to bind the recognition agent to a recognition site on the surface of the cell and thereafter introducing the substance into the cell.

* * * * *